US006623763B2

(12) United States Patent
Asmussen et al.

(10) Patent No.: US 6,623,763 B2
(45) Date of Patent: Sep. 23, 2003

(54) PHARMACEUTICAL PREPARATION ADHERING TO THE SKIN, IN PARTICULAR A TRANSDERMAL THERAPEUTIC SYSTEM FOR THE RELEASE OF 17-β-ESTRADIOL TO THE HUMAN ORGANISM

(75) Inventors: Bodo Asmussen, Bendorf-Sayn (DE); Michael Horstmann, Neuwied (DE)

(73) Assignee: LTS Lohmann Therape-System AG, Andemach (DE)

( * ) Notice: Subject to any disclaimer, the term of this patent is extended or adjusted under 35 U.S.C. 154(b) by 148 days.

(21) Appl. No.: 09/885,132

(22) Filed: Jun. 19, 2001

(65) Prior Publication Data

US 2001/0043944 A1 Nov. 22, 2001

Related U.S. Application Data

(63) Continuation-in-part of application No. 09/101,720, filed as application No. PCT/EP96/05822 on Dec. 23, 1996, now Pat. No. 6,267,982.

(51) Int. Cl.⁷ .......................... A61F 13/02; A61L 15/16
(52) U.S. Cl. .................... 424/489; 424/449; 514/169
(58) Field of Search ................. 424/448, 449; 514/169

(56) References Cited

U.S. PATENT DOCUMENTS 4,863,738 A   9/1989  Taskovich
6,267,982 B1 * 7/2001  Asmussen et al. .......... 424/448

FOREIGN PATENT DOCUMENTS

DE   44 29 664    2/1996
EP   0421454      10/1990   ........... A61L/15/16
WO   WO 93/10772  6/1993

OTHER PUBLICATIONS

Kuhnert–Brandstätter, "Thermoanalytische und IR–spektroskopische Untersuchungen an verschiedenen Kristallformen von Arzneistoffen aus der Östradiol– und Androstangruppe." *Scienta Pharmaceutica* 44 (3): 177–190, 1976.
*SCRIP* No. 2026, May 19, 1995 p 23.
Deutsche Zentralbibliothek Für Medizin: Nicht Vorhanden.

* cited by examiner

*Primary Examiner*—Jose' G. Dees
*Assistant Examiner*—Konata M George
(74) *Attorney, Agent, or Firm*—Janet Sleath; ANn W. Speckman

(57) ABSTRACT

A pharmaceutical preparation adhering to the skin, in particular a transdermal therapeutic system, for the release of the active substance 17-β-estradiol, contained therein in dissolved form being between its saturation concentration in equilibrium with a gas phase of less than 10% relative air humidity and its saturation concentration in equilibrium with a gas phase of more than 90% relative air humidity, in all matrix levels and, if present, also in an adhesive layer, characterized in that the estradiol quantity contained in in the preparation amounts to at least three times the saturation solubility measured at 95% relative air humidity, and that the air enclosed in the package is adjusted to a relative air humidity between 5% and below 0.5%.

13 Claims, No Drawings

PHARMACEUTICAL PREPARATION ADHERING TO THE SKIN, IN PARTICULAR A TRANSDERMAL THERAPEUTIC SYSTEM FOR THE RELEASE OF 17-β-ESTRADIOL TO THE HUMAN ORGANISM

REFERENCE TO RELATED APPLICATIONS.

This application is a continuation-in-part application of U.S. patent application Ser. No. 09/101,720, filed Mar. 17, 1999, now U.S. Pat. No. 6,267,982, which was the National Stage of International Application No. PCT/EP96/05822 filed Dec. 23, 1996.

The present invention relates to a pharmaceutical preparation adhering to the skin, in particular a transdermal therapeutic system, for the release of 17-β-estradiol and optionally further active substances through the skin to the human organism.

Pharmaceutical preparations contacting the skin include, for example, ointments, creams, lotions, and also drug-containing patches, these have been introduced on the market for some time under the name "transdermal therapeutic systems" (TTS) to treat several diseases.

In the meantime, TTSs comprising the active substance 17-β-estradiol have also been on the market as a therapeutic agent for climacteric complaints, and, for a short time, also against osteoporosis, proving successful in therapy.

In several cases, however, the insufficient capability of the active substance to permeate through the skin has become apparent as a disadvantage of prior art systems. This cannot be increased beyond a certain limit, the so-called "saturation flow", although numerous galenic measures with respect to the TTS-construction have been taken (use of multilayer systems, use of controlling membranes, variations of the active substance concentration, modification of the base polymer, and the like).

The finding that the transdermal flow of an active substance from the solid, finely dispersed phase cannot be increased further, even if high-dissolving vehicles are used, can already be found in the trailblazing works of Higuchi (e.g., T. Higuchi: Physical Chemical Analysis of percutaneous absorption process from creams and ointments, J. Soc. Cosmetic Chem. 11 p. 85–97 (1960). However, for many active substances there is the possibility of adding so-called "enhancers" to the TTS during its production. In general, these are liquid additives improving the absorption properties of human skin so that the active substance can be absorbed from a sufficiently small TTS-surface.

In particular readily volatile enhancers, e.g., ethanol frequently used for the active substance 17-β-estradiol, cause problems due to extreme softening of the patches' adhesive layers, therefore they require additional bulky compartments in the system, rendering the TTS unacceptably thick or voluminous. Finally, any additional non-polymeric additive involves the risk of intolerance phenomena on the skin, possibly even that of sensitization. The addition of less volatile, however, mostly less active enhancers (e.g., glycerol esters, cyclic amides, eucalyptol) makes it possible to produce matrix systems comprising the active substance and absorption-promoting components in one or several monolithic layers. However, the adhesive strength of the patch remains unsatisfactory.

U.S. Pat. No. 4,863,738 represents one of many examples claiming the application of an active substance, e.g., 17-β-estradiol, together with an enhancer (in this case glycerol monooleate) in an optional concentration within a TTS-matrix.

According to the art, these TTSs do not permit a satisfactory therapy, either because the chosen enhancers have a poor skin tolerance, or the systems must have unacceptably large surfaces owing to insufficient active substance flow through the skin.

Dissolving more active substance molecularly disperse in the TTS than corresponds to the saturation solubility might be another possibility of increasing the active substance flow through the skin. With the degree of supersaturation of these systems the permeation rate through the skin is increased to the same extent. However, since supersaturated physical states are thermodynamically unstable, these forms of administration are not stable in storage. Spontaneous, unforeseeable precipitations of active substance particles will take place within months, or not later than years, so that the flow rate through the skin gradually decreases to the saturation flow level and a great deal of the initially existent therapeutic activity is lost.

The systems described in EP 0 421 454 comprise 17-β-estradiol in an acrylate polymer under addition of "crystallization inhibitors" and tackifying resins. Swelling agents are contained to give protection against premature loss of adhesive force.

A completely different way of avoiding thermodynamic instability js opened up in DE 42 37 453. It describes a transdermal therapeuticsystem having an active substance concentration ranging between the saturation solubility under moist conditions and that under dry conditions. A maximum ambient humidity of 10% is meant by "dry" conditions, and the achieved increase of skin permeation is stated to be about 50%.

It is the object of the present invention to provide a pharmaceutical preparation which, as compared to the prior art, results in higher active substances flows through the skin and does not undergo activity losses owing to recrystallization or active substance precipitation during storage.

According to the present invention this object is achieved in a pharmaceutical preparation according to the introductory part of claim 1 by the characterizing features stated in claim 1, by the fact that the estradiol amount contained in the preparation amounts to at least three times the saturation solubility amount measured at 95% atmospheric humidity, and that the air present in the package is adjusted to a relative air humidity of below 5%, preferably below 2% relative air humidity.

At room temperature and a relative air humidity between 20 and 60%, 17-β-estradiol is not present in an anhydric modification (I and 11), but as a semihydrate (Busetti and Hospital, Acta Cryst. 1972, B28, 560). Owing to the layered structure stabilized via hydrogen bridges, and because of the diffusional compactness of the crystal compound, the hydrate can be subjected to a short-term heat treatment to temperatures of up to 170° C. without decomposition (Kuhnert-8randstatter and Winkler (1976), Scientia Pharmaceutica 44 (3), 177–190).

With decreasing partial water vapor pressure, on the other hand, 17-β-estradiol has a higher solubility in some polymers, particularly in acrylate copolymers and in mixtures of rubbers and resins, polyvinyl acetate, polyvinyl alcohols, in polyvinyl pyrrolidone and mixtures or copolymers thereof, as well as in silicone polymers.

The fact that 17-β-estradiol, under the conditions indicated above, has a higher solubility in some polymers, particularly in acrylate copolymers, has already been known from DE 42 37 453; however, the extent of solubility increase to more than three times the amount has not been expected and is most surprising (Example 1), even in consideration of the art. According to Fick's law, higher active substance concentrations in a TTS with otherwise same conditions increase the diffusion flow through the skin; for this reason, such a concentration increase in transdermal therapeutic systems is very advantageous. Thus, preparations manufactured according to the present invention can develop the same efficacy as prior-art systems, but with a smaller surface. However, absolute dry storage conditions are required to stabilize these properties.

These can preferably be ensured by gasproof and moistureproof packages, and by inserting moisture-absorbing products into the packing.

The above-described invention may be realized in pharmaceutical preparations in different manners.

In an ointment, 17-β-estradiol is homogeneously distributed as an anhydrate or semihydrate according to usual methods by stirring under heating and adding to the ointment base an estradiol solution in a solvent, or by dispersing the micronized active substance. The simplest form of a percutaneous skin-adherent pharmaceutical preparation is a single-layer matrix system whose matrix, in addition to its function of delivering active substances, is pressure-sensitive adhesive at the same time, rendering an adhesive layer superfluous. However, the system may also be divided into several layers of the same or different composition and function.

If a membrane, which is poorly permeable to estradiol, is placed between such a matrix and a skin-facing adhesive layer, an active substance release is obtained which is controlled to a greater extent by the patch than by the skin. Such an active substance release may be advantageous if a very narrow margin of daily dosage is desired.

For use in the matrix layer or layers and, if present, in the adhesive layer,
mixtures of rubbers and resins;
polyvinyl acetate, polyvinyl alcohols, polyvinyl-pyrrolidone and mixtures or copolymers thereof; and
silicone polymers
are especially suitable as base materials. However, many other base materials, which are compatible with the skin, are also suitable. The aforementioned materials can also be used as mixtures or in combination.

Rubbers may be natural rubber as well as synthetic rubbers, including polystyrene-based rubbers such as styrene-isoprene-styrene (SIS) copolymers or styrene-butadiene-styrene (SBS) copolymers, polyisobutylene, polybutene, polyisoprene, silicone rubbers, and the like.

Resins which are particularly suitable are colophony (rosin) or colophony derivatives (rosin derivatives) as, for example, esters of colophony, rosin alcohols, hydrogenated colophony, and derivatives thereof, derivatives of abietyl alcohol and of β-pinene, as well as hydrocarbon resins (saturated or unsaturated), e.g., polyterpene resins, as well as petroleum rsins, coumarone-indene resins, terpene phenol resins. However, the invention is not limited to the selection of the above-mentioned resins. Generally, all types of resins may be used which asr known to the skilled person as "tackifying resins."

Silicone polymers may be present in said layer(s) in the form of silicone adhesives or, if present in the matrix layer or layers, as more or less rigid gel-like or rubber-like polymerisates. For example, pressure-sensitive adhesives based on a polydimethylsiloxane structure can be used.

Acrylate copolymers are copolymers formed by radical polymerization of esters of acrylic acid and/or of methacrylic acid with $C_1$ to $C_{18}$-alcohols, dimethylaminoethanol, or other suitable alcoholic reactants, vinyl acetate, vinyl pyrrolidone, styrene, butadiene, acrylonitrile, or other suitable monomers with a vinyl group.

To render the system softer, 1,2-propanediol, 1,3-butylene glycol, 1-hexadecanol may be added, for example; or also 2-hydroxyfatty alcohols, 2-octyl dodecanol, 2-propanol, benzyl alcohol, cetylstearyl alcohol, diethylene glycol, dipropylene glycol, dodecanol, ethanol, glycerol, hexanediol, octanol, oleyl alcohol, panthenol, phenylethanol, polyethylene glycols, or polypropylene glycols; or fatty acids, such as, capric, linoleic, lauric, myristic acid, n-valeric acid, pelargonic acid; and also physiologically acceptable organic acids, such as, 3-phenylpropionic acid, acetic acid, adipic acid, benzoic acid, oleic acid, salicylic acid, or their salts well tolerated by the skin. Other compounds of this kind include—without claiming completeness—sulfates and sulfonates of fatty acids, esters of the formula $[CH_3(CH_2)_m COO]R$, wherein m represents a number of 8 to 16, n 1 or 2, and R a short-chain alkyl chain; triglycerides, phthalates, sulfoxides, or amides.

Furthermore, the addition of up to 40% wt. of fillers, such as titanium dioxide, zinc oxide, chalk, activated charcoal, finely divided silicium dioxide, etc., does by no means impair the function of the pharmaceutical preparations according to the present invention, and may be advantageous with respect to the cohesion of the finished product.

Typically, the transdermal systems further comprise a film-like removable protective layer which covers the adhesive layer during storage and which is removed before the system is applied to the skin of a patient. The material used for the removable protective layer is of less importance for the function of the transdermal system. The protective layer may, for instance, consist of a polyester material, e.g., polyethylene terephthalate. However, other skin-compatible plastics may also be used, such as polyvinyl chloride, polyvinylidene chloride, ethylene vinylacetate, polyethylene, polypropylene, cellulose derivatives, laminates of those materials, and many other materials may be used. In particular cases, the protective layer could be metallized or treated by vapor-plating with other diffusion-blocking additives, such as silicon dioxide, aluminium oxide, and the like. In any case, the surface facing the adhesive matrix must be treated with dehesive (release) materials, such as silicones or fluorine-containing compounds, so that the protective layer remains easily removable.

The thickness of the film-like, removable protective layer normally amounts to about 40 to 200 μm; however, for special purposes, it may also be thicker or thinner than that.

The present invention will be illustrated in greater detail in the following with reference to Examples.

EXAMPLE 1

Production of a System According to the Present Invention.

3.6 g 17-β-estradiol-semihydrate, micronized, and 150.4 g solution of an acrylate copolymer with a solid content of 37.5% are stirred at room temperature in a cylindrical glass vessel until a homogenous suspension results, subsequently this is coated on a siliconized polyester film having a thickness of 100 μm in such a manner that a layer thickness of 61 g/m² (relative to the solvent-free portion) results. This results in a portion of 6% (w/w) estradiol in the active substance-containing layer. The layer is dried for 10 minutes at 25° C. and for 15 minutes at 90° C., causing complete dissolution of the active substance under the influence of the heat. After that, a polyester film having a thickness of 15 μm is applied (laminated) as backing layer.

By punching using a steel rule cutting die, transdermal systems of 16 cm² are obtained which are stored:

a) at 31° C./70% relative humidity; and
b) at about 20–30° C. (room temperature), 0% relative humidity.

After 3 weeks of storage, the samples according to condition a) (prior art) show complete, macroscopically detectable crystallizations. In contrast to this, the samples of condition b) (according to the present invention) remain completely dissolved

EXAMPLE 2

Production of a System (Comparative Example).

0.9 g 17-β-estradiol-semihydrate, micronized, and 157.6 g solution of an acrylate copolymer with a solids content of 37.5% are stirred at room temperature in a cylindrical glass vessel until a homogenous solution results, and are subsequently coated on a siliconized polyester film having a thickness of 100 μm in such a manner that a layer thickness of 58 g/m² (relative to the solvent-free portion) results.

This results in a portion of 1.5% (w/w) freely dissolved estradiol in the active substance-containing layer. The layer is dried for 10 minutes at 25° C. and for 15 minutes at 90° C. After that, a polyester film having a thickness of 15 μm is applied (laminated) as backing layer.
By punching using a steel rule cutting die, transdermal systems of 16 cm² are obtained which are stored a) at 31° C./70% relative humidity, b) at about 20–30° C. (room temperature), 0% relative humidity.

After 3 weeks of storage, the samples according to condition a) show fine, microscopically easily detectable crystallizations. The samples of condition b), however, remain completely dissolved.

EXAMPLE 3

Matrix Layer and Backing 10 g styrene-isoprene-styrene block copolymer (Cariflex TR 1107; from: Shell) is completely dissolved in 25 g naphtha having a boiling range of between 80 and 100° C. 300 mg 17-β-estradiol semihydrate (dissolved in 12 g ethyl acetate) is added; the mass is mixed until homogeneous and is then coated onto a 15 μm polyester (polyethylene terephthalate) film, using a gap width of about 150 μm, such that a uniform layer having a weight per unit area of 40 g/m² results after drying at 35° C. for 1 h and, subsequently, at 100° C. for 1 h, and finally at 140 C fort 20 min.

Adhesive Layer

In a separate operation, a solution of 3 g hydrogenated colophony glycerol ester resin (Staybelite Ester 5E; from: Hercules) and 7 g polyisobutylene (Oppanol B 30; from: BASF) is prepared in 10 g ethyl acetate and 10 g naphtha (having a boiling range between 80 and 100° C.). 0.12 g 17-β-estradiol semihydrate is added which dissolves completely at room temperature. Using a gap width of about 100 μm, the mass is coated onto an anti-adhesive polyester (polyethylene terephthalate) film serving as protective layer, such that a uniform layer having a weight per unit area of 23 g/m² results after drying at 35° C. for 30 min., thereafter at 60° C. for 15 min and finally at 120° C. for 20 min.

The thus produced matrix and adhesive layers are then laminated on top of each other, upon which they spontaneously form a composite (or laminate) which cannot be separated manually, the polyethylene terephthalate layers forming the outer surfaces of the sandwich structure. From this composite—comprising backing layer, matrix layer, adhesive layer and protective layer (release liner)—, individual transdermal systems are punched out, having a defined contour and size, and the outer rims are removed. Each administration form is packed into an individually sealed bag.

For applying the administration form (transdermal system) onto the skin, the user removes it from the package, peels off the protective layer (release liner) and sticks the administration form onto a suitable site of his or her skin. Optionally, the polyester film covering the matrix layer on the outside may be detached after patch application in order to improve wearing properties.

EXAMPLE 4

300 mg 17-β-estradiol semihydrate are dissolved in 10 g silicone adhesive (BIO-PSA Q7–4302; Dow Corning), diluted with ethyl acetate to a solids content of 30%. This mass is then mixed homogeneously and, using a gap width of about 150 μm, is coated onto a 15 μm polyester film (as a backing layer) such that a uniform layer having a weight per unit area of 40 g/m² results after drying at 35° C. for 1 h, and, subsequently, at 100° C. for 1 h, and, finally, at 140° C. for 20 min. After drying, an anti-adhesive polyester film (serving as release liner) is laminated to the adhesive surface.

From the resulting composite or laminate, consisting of backing layer, adhesive layer and anti-adhesive release liner, individual administration forms (transdermal systems) having a defined shape and size are punched out in a manner known to the artisan. Each administration form is packed individually into a sealed bag.

The uniform supply of estradiol has proved to be effective for the prophylaxis of the Alzheimer's and Parkinson's disease (Scrip No.2026, p. 23; May 19, 1995). Therefore, this indication involves an ethically particularly significant application of the above-described skin-adherent pharmaceutical preparations.

What is claimed is:

1. A pharmaceutical preparation for adhering to the skin, for the release of the active substance 17-β-estradiol, said preparation comprising one or more polymer(s) in which 17-β-estradiol semihydrate or anhydrate is dissolved by drying, said active substance being present in a concentration of at least three times the saturation solubility concentration measured at 95% relative air humidity, said polymer (s) being selected from the group comprising mixtures of rubbers and resins;
polyvinyl acetate, polyvinyl alcohols, polyvinyl-pyrrolidone and mixtures or copolymers thereof; and
silicone polymers
and wherein the pharmaceutical preparation is contained in a moisture-tight package having an amount of air enclosed within, wherein the enclosed air within the package is adjusted to a relative air humidity below 5%.

2. The preparation according to claim 1, wherein said preparation is a transdermal therapeutic system.

3. The preparation according to claim 1, wherein said preparation comprises a pressure-sensitive adhesive layer and a non-tack backing layer facing away from the skin.

4. The preparation according to claim 1, wherein said polymer(s), at 0.1% relative humidity, comprise(s) at least 6% (w/w) 17-β-estradiol in dissolved form.

5. The preparation according to claim 1, wherein said polymer(s), at 0.1% relative humidity, comprise(s) at least 8% (w/w) 17-β-estradiol in dissolved form.

6. The preparation according to claim 1, wherein said preparation additionally comprises an adhesive layer, and the adhesive layer contains 17-β-estradiol in dissolved form.

7. The preparation according to claim 1, wherein the air enclosed in the package is adjusted by the addition of a desiccant.

8. The preparation according to claim 7, wherein the air enclosed in the package is adjusted to a relative air humidity below 2%.

9. The preparation according to 7, wherein the air enclosed in the package is adjusted to a relative air humidity below 0.5%.

10. A process for the production of primary-packaged, skin-adherent pharmaceutical preparations according to claim 1, comprising preparing a solution or dispersion of 17-β-estradiol semihydrate in a polymer, followed by coating it onto a film-like, anti-adhesive base material, drying the layer and applying a backing layer which is impermeable to active substances and moisture, and separating by blanking and film cutting, characterized in that drying is effected by intermediate storage at an air humidity of below 5% relative humidity, up to complete dissolution of the contained estradiol, and by packing into gas-tight packages, optionally with addition of a moisture-absorbing material.

11. The process according to claim 10, wherein said drying is effected by immediate storage at an air humidity of below 2% relative humidity.

12. The process according to claim 10, wherein said drying is effected by immediate storage at an air humidity of below 0.5% relative humidity.

13. A method of treatment or prophylaxis of menopausal symptoms, osteoporosis or Alzheimer's disease, comprising applying the pharmaceutical preparation according to claim 1 to the skin of a subject.

* * * * *